United States Patent

Masaki et al.

(10) Patent No.: US 8,885,033 B2
(45) Date of Patent: Nov. 11, 2014

(54) ENDOSCOPE SYSTEM

(71) Applicant: Olympus Medical Systems Corp., Tokyo (JP)

(72) Inventors: Takahiro Masaki, Kawasaki (JP); Yusuke Yabe, Chofu (JP); Tomoya Takahashi, Hachioji (JP); Masato Toda, Hachioji (JP); Yutaka Shirota, Sagamihara (JP); Daisuke Akiyama, Fuchu (JP); Koji Omori, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/964,445

(22) Filed: Aug. 12, 2013

(65) Prior Publication Data

US 2014/0049624 A1    Feb. 20, 2014

Related U.S. Application Data

(63) Continuation of application No. PCT/JP2013/054954, filed on Feb. 26, 2013.

(30) Foreign Application Priority Data

Mar. 29, 2012   (JP) .................................. 2012-076989

(51) Int. Cl.
*A61B 1/04*    (2006.01)
*A61B 1/00*    (2006.01)
*A61B 1/06*    (2006.01)
*G02B 23/24*   (2006.01)
*H04N 7/18*    (2006.01)

(52) U.S. Cl.
CPC ........... *A61B 1/0638* (2013.01); *A61B 1/00006* (2013.01); *H04N 7/18* (2013.01); *A61B 1/00009* (2013.01); *G02B 23/24* (2013.01)
USPC ............................................ 348/68; 600/109

(58) Field of Classification Search
CPC ................... A61B 1/0638; A61B 1/05; H04N 2005/2255; H04N 5/2354
See application file for complete search history.

(56) References Cited

U.S. PATENT DOCUMENTS 6,545,703 B1 *  4/2003  Takahashi et al. ............. 348/69
6,975,898 B2 * 12/2005  Seibel .......................... 600/473

(Continued)

FOREIGN PATENT DOCUMENTS

EP    2 157 356 A1    2/2010

(Continued)

*Primary Examiner* — Joseph Ustaris
*Assistant Examiner* — Zhubing Ren
(74) *Attorney, Agent, or Firm* — Scully, Scott, Murphy & Presser, PC

(57) ABSTRACT

Provided is an endoscope system including: a light source apparatus detecting which color LED fails by a color sensor; a scope that irradiates a subject with illuminating light and takes in an optical image of the subject; a CCD that picks up an image of the optical image of the subject; a video processor that processes the picked up image; and a monitor that displays a processed image, wherein if a failure of any of the LEDs is detected by the color sensor, the light source apparatus generates illuminating light using LEDs of colors other than a color of the light-emitting device for which the failure is detected, and wherein the video processor switches image processing to image processing according to a color of the LED for which the failure is detected.

8 Claims, 8 Drawing Sheets

(56) References Cited

U.S. PATENT DOCUMENTS

| | | | |
|---|---|---|---|
| 7,159,782 B2* | 1/2007 | Johnston et al. | 235/462.45 |
| 2009/0118578 A1 | 5/2009 | Takasugi et al. | |
| 2010/0194290 A1 | 8/2010 | Hanano | |

FOREIGN PATENT DOCUMENTS

| | | |
|---|---|---|
| JP | 2002-045330 A | 2/2002 |
| JP | 2006-061567 A | 3/2006 |
| JP | 2006-087764 A | 4/2006 |
| JP | 2006-136453 A | 6/2006 |
| JP | 2007-014422 A | 1/2007 |
| JP | EP 1 889 563 A1 | 2/2008 |
| JP | 2008-305710 A | 12/2008 |
| JP | 2012-217484 A | 11/2012 |

* cited by examiner

ENDOSCOPE SYSTEM

CROSS REFERENCE TO RELATED APPLICATION

This application is a continuation application of PCT/JP2013/054954 filed on Feb. 26, 2013 and claims benefit of Japanese Application No. 2012-076989 filed in Japan on Mar. 29, 2012, the entire contents of which are incorporated herein by this reference.

BACKGROUND OF THE INVENTION

1. Field of the Invention

The present invention relates to an endoscope system in which illuminating light, which irradiates a subject from an endoscope, is emitted from light-emitting devices of a plurality of colors in a light source apparatus.

2. Description of the Related Art

As light source apparatuses for irradiating a subject with illuminating light from an endoscope, those using light-emitting devices such as LEDs have been proposed.

FIG. 10 is a diagram illustrating a configuration of a conventional endoscope system using LEDs as light sources.

An endoscope system 101 includes a scope 2, a light source apparatus 3, a video processor 4, a monitor 5 and a communication cable 6.

The light source apparatus 3 uses light-emitting devices that are a red LED (R-LED) 23r, a green LED (G-LED) 23g and a blue LED (B-LED) 23b as light sources, and includes an LED drive section 22 for supplying power to these LEDs to drive the LEDs, and a control section 21 that controls the LED drive section 22 based on information on a brightness of an object, which is to be inputted from the video processor 4 via the communication cable 6, to adjust intensities of light emitted from the LEDs of the respective colors.

Light emitted from the LEDs 23r, 23g and 23b in the light source apparatus 3 irradiates a proximal end of a light guide 11 in the scope 2 via an optical system. The illuminating light is conveyed inside the light guide 11, and irradiates a subject via a lens 12 for illumination, which is disposed at a distal end of an insertion portion of the scope 2.

An optical image of the illuminated subject is converted into an electrical signal by a CCD 13, which is an image pickup device disposed in a distal end portion of the insertion portion of the scope 2, and transmitted to the video processor 4.

Based on the electrical signal received from the CCD 13, the video processor 4 generates an image signal for providing display on the monitor 5, and generates brightness information and transmits the brightness information to the control section 21 in the light source apparatus 3 via the communication cable 6.

If red light emitted from the red LED 23r, green light emitted from the green LED 23g and blue light emitted from the blue LED 23b in the light source apparatus 3 are combined by, for example, the optical system in the light source apparatus 3, as illustrated in FIG. 2 relating to the present invention, white illuminating light WL can be generated.

However, even if frame-sequential illumination in which LEDs of respective colors are put on in turn at different times within one frame is performed as illustrated in FIG. 3 relating to the present invention instead of combination of light of respective colors via the optical system in the light source apparatus 3, an image displayed on a monitor as a result of combination performed in the video processor is an object image effectively provided by illumination with white illuminating light.

For example, in Japanese Patent Application Laid-Open Publication No. 2002-45330, paragraph [0044] discloses that an illumination unit 110 includes three light sources that emit white light Lw for normal image, excitation light Lr for autofluorescent image and reference light Ls for reference image, respectively, and paragraph [0013] discloses that if excitation light emitting means or reference light emitting means operates abnormally, illuminating light is emitted from illuminating light emitting means, image pickup means is switched to a state for picking up a normal image and display means is switched to a state for displaying a normal image.

The technique disclosed in Japanese Patent Application Laid-Open Publication No. 2002-45330 is a technique that if special illumination such as that with, e.g., excitation light fails, the illumination is switched to normal illumination.

SUMMARY OF THE INVENTION

An endoscope system according to an aspect of the present invention includes: a light source apparatus including light-emitting devices of a plurality of colors, and a failure detection section that detects which color light-emitting device fails from among the light-emitting devices of the plurality of colors; an endoscope that irradiates a subject with illuminating light generated by the light source apparatus and takes in an optical image of the subject; an image pickup device that picks up an image of the optical image of the subject; a video processor that processes the image picked up by the image pickup device; and a monitor that displays the image processed by the video processor, and if a failure of any of the light-emitting devices is detected by the failure detection section, the light source apparatus generates the illuminating light using light-emitting devices of colors other than a color of the light-emitting device for which the failure is detected from among the plurality of light-emitting devices, and if a failure of any of the light-emitting devices is detected by the failure detection section, the video processor switches image processing to image processing according to a color of the light-emitting device for which the failure is detected, the image processing being different from that when the failure of the light-emitting device is not detected.

DETAILED DESCRIPTION OF THE PREFERRED EMBODIMENTS

Embodiments of the present invention will be described below with reference to the drawings.

[Embodiment 1]

Figure 1:
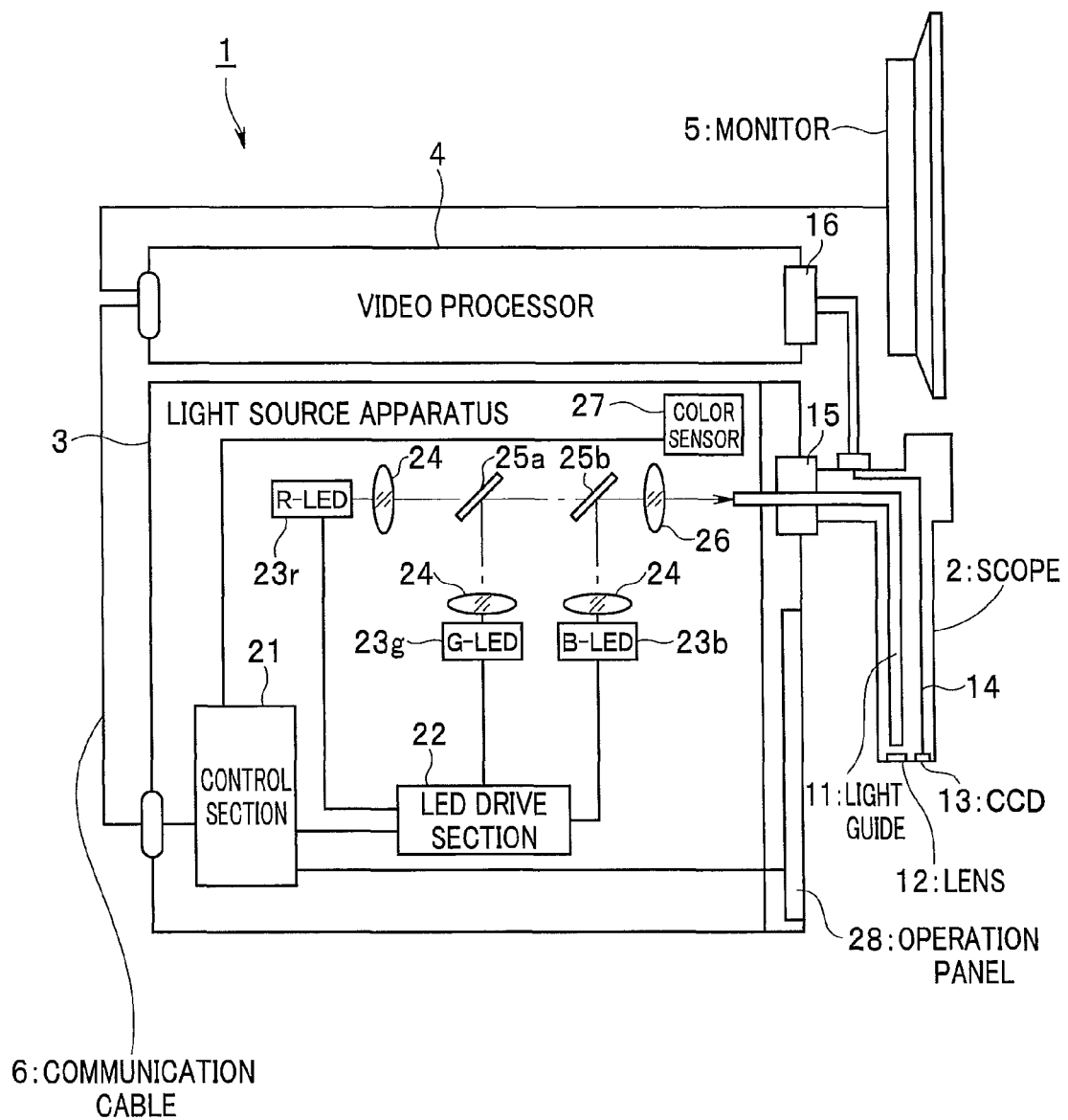
FIG. 1 is a diagram illustrating a configuration of an endoscope system according to Embodiment 1 of the present invention.
Figure 2:
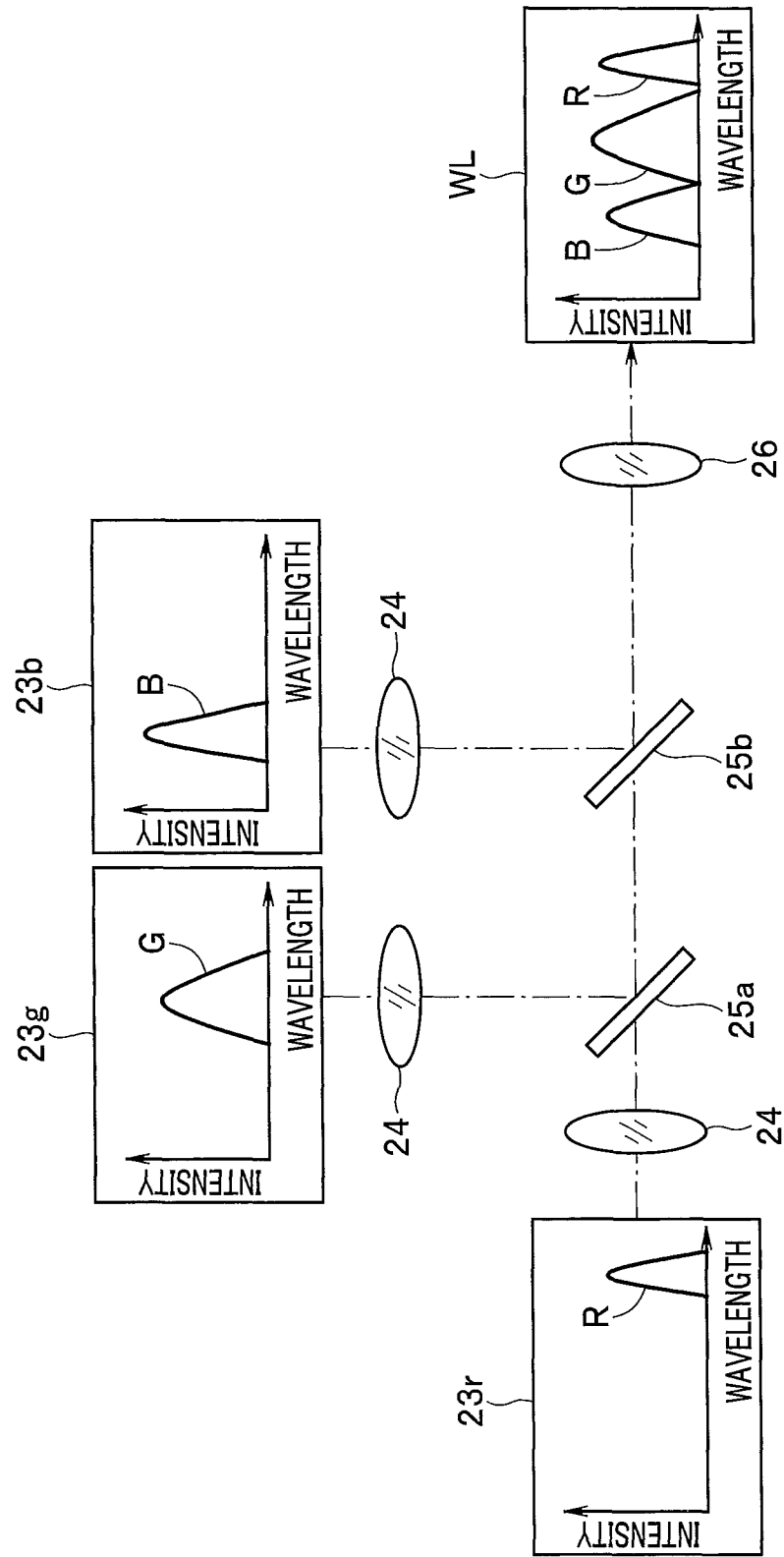
FIG. 2 is a diagram illustrating states of spectra of light emitted from LEDs of respective colors in a light source apparatus in Embodiment 1.

FIGS. 1 to 4 illustrate Embodiment 1 of the present invention: FIG. 1 is a diagram illustrating a configuration of an endoscope system, and FIG. 2 is a diagram illustrating states of spectra of light emitted from LEDs of respective colors in a light source apparatus.

An endoscope system 1 includes a scope 2, a light source apparatus 3, a video processor 4, a monitor 5 and a communication cable 6.

The light source apparatus 3 uses light-emitting devices of a plurality of colors as light sources, the light-emitting devices of the plurality of colors include light-emitting devices for emitting light of three colors forming white light, more specifically, a red LED (R-LED) 23r, which is a red (R) light-emitting device, a green LED (G-LED) 23g, which is a green (G) light-emitting device, and a blue LED (B-LED) 23b, which is a blue (B) light-emitting device. Emission spectra of the respective light-emitting devices differ from one another, and as illustrated in FIG. 2, light emitted from the red LED 23r has a spectrum in a band of red light R, light emitted from the green LED 23g has a spectrum in a band of green light G, and light emitted from the blue LED 23b has a spectrum in a band of blue light B.

The LED drive section 22 provided in the light source apparatus 3 supplies power to the red LED 23r, the green LED 23g and the blue LED 23b to drive the red LED 23r, the green LED 23g and the blue LED 23b, respectively.

The control section 21 provided in the light source apparatus 3 controls the LED drive section 22 so as to adjust intensities of respective light emitted from the red LED 23r, the green LED 23g and the blue LED 23b. Such control by the control section 21 is performed based on information on a brightness of an object, which is obtained by means of communication with the video processor 4 via the communication cable 6.

In the light source apparatus 3, three collimator lenses 24, two dichroic filters 25a and 25b and one condenser lens 26 are provided as an optical system that conveys illuminating light.

The three collimator lenses 24, which are disposed on respective optical paths of respective light emitted from the red LED 23r, the green LED 23g and the blue LED 23b, and each make incoming light exit in the form of collimated light.

The first dichroic filter 25a transmits red light R from the red LED 23r, and reflects green light G from the green LED 23g.

The second dichroic filter 25b transmits red light R from the red LED 23r and green light G from the green LED 23g, and reflects blue light B from the blue LED 23b.

The condenser lens 26 collects a collimated light flux from the second dichroic filter 25b onto an incident end face of a proximal end of the light guide 11 in the scope 2.

When three light-emitting devices, that is, the red LED 23r, the green LED 23g and the blue LED 23b are caused to emit light simultaneously, if the respective emission intensities fall within respective predetermined ranges, light exiting from the condenser lens 26 is white illuminating light WL with all of three colors, i.e., RGB contained as illustrated in FIG. 2.

Furthermore, in the light source apparatus 3, a color sensor 27 is provided as a failure detection section that detects a failure of any of the light-emitting devices. The color sensor 27 is disposed at, for example, a position where leaked light, which does not fall on the incident end face of the light guide 11, in the light flux exiting from the condenser lens 26 is detected (for example, in the vicinity of a scope socket to which a light guide connector 15 of the scope 2 is connected). The color sensor 27 performs color sensing to detect respective optical intensities of the red light R, the green light G and the blue light B, and outputs a result of the detection to the control section 21.

Where an emission intensity of any of three LEDs cannot be made to fall within the respective predetermined ranges even if the LED drive section 22 performs driving of three LEDs within respective specification ranges, the control section 21 determines that the LED fails. In other words, light-emitting device failures include not only failures to emit light, but also failures to emit predetermined light such as failures to maintain a predetermined level of emission intensity.

Also, an operation panel 28 provided in the light source apparatus 3 is provided for a user to perform an operation of the light source apparatus 3, and enables, e.g., an operation to turn on/off power of the light source apparatus 3 and an operation to set an illumination mode. An illumination mode inputted from the operation panel 28 is transmitted to the video processor 4 via the control section 21 and the communication cable 6 to perform image processing according to an observation mode that corresponds to the illumination mode.

The scope 2, which is an endoscope that receives supply of illuminating light from such light source apparatus 3, includes the light guide 11, a lens 12, a CCD 13, a signal wire 14, the light guide connector 15 and a video connector 16.

The light guide 11 includes a proximal end extending from the light guide connector 15, and when the light guide connector 15 is connected to the light source apparatus 3, light from the above-described condenser lens 26 is collected onto the incident end face of the proximal end of the light guide 11.

The light guide 11 is inserted through the inside of the insertion portion of the scope 2 to the distal end portion, and makes illuminating light exit from an exit face of the distal end. On an optical path of illuminating light at the distal end of the scope 2, the lens 12 for illumination is disposed. Consequently, illuminating light from the light source apparatus 3 is conveyed inside the light guide 11 and irradiates a subject from the distal end of the insertion portion via the lens 12.

An optical image of the subject which has been irradiated with the illuminating light is taken in via a non-illustrated objective lens disposed at the distal end of the insertion portion of the scope 2, and is formed on the CCD 13, which is an image pickup device. The CCD 13 may be a color image pickup device in which a color filter array or the like is disposed; however, in the present embodiment, the CCD 13 is a monochromatic image pickup device that receives frame-sequential illuminating light (however, the illumination is not limited to frame-sequential illumination). Then, the CCD 13 performs image pickup to convert the optical image of the subject into an electrical signal, and transmits the electrical signal to the video processor 4 to which the video connector 16 is connected, via the signal wire 14.

The video processor 4 synchronizes images of respective colors received from the CCD 13 to generate a color image signal, and performs image processing such as color balance adjustment, gamma conversion and color conversion, and then converts the resulting image signal into a signal format for display on the monitor 5 and outputs the resulting image signal to the monitor 5. Consequently, a color image of the object is displayed on the monitor 5.

Also, the video processor 4 extracts, for example, a luminance signal from the received image of each color and generates brightness information based on the extracted luminance signals. The brightness information generated by the video processor 4 as described above is transmitted to the control section 21 in the light source apparatus 3 via the communication cable 6 connecting the video processor 4 and the light source apparatus 3.

As described above, the control section 21 performs control of the emission intensities of the LEDs of the respective colors via the LED drive section 22 based on the received brightness information. Also, the control section 21, based on output values from the color sensor 27, not only detects a failure of any of the LEDs, but also performs color balance adjustment, that is, adjustment of an emission intensity balance among the red LED 23*r*, the green LED 23*g* and the blue LED 23*b*.

Figure 3:
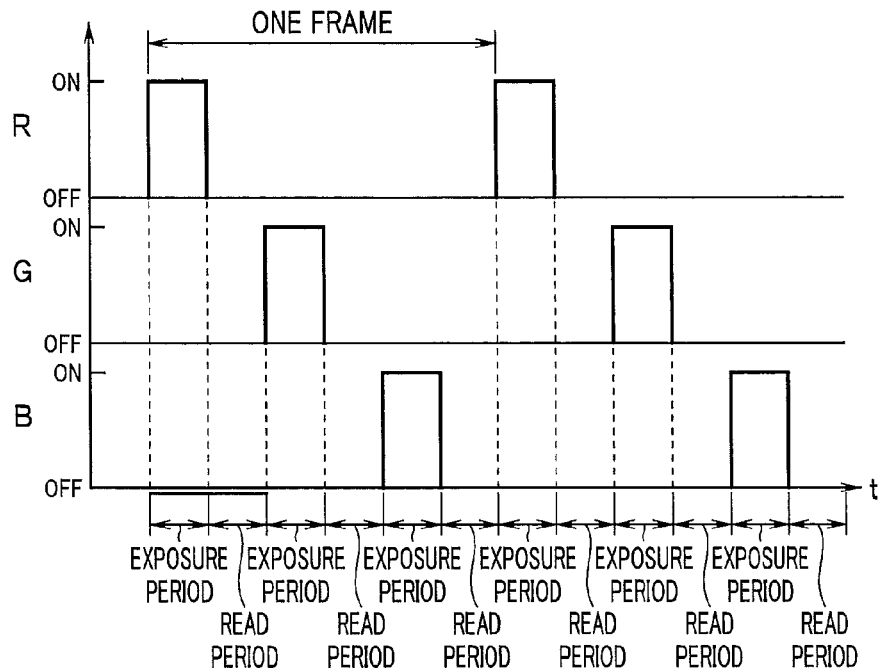
FIG. 3 is a timing chart indicating light emission timings for LEDs of respective colors when frame-sequential illumination is performed in Embodiment 1.

Next, FIG. 3 is a timing chart indicating light emission timings for LEDs of respective colors when frame-sequential illumination is performed.

The CCD 13 alternately performs an exposure-period operation to receive light and accumulate a charge, and a read-period operation to sequentially read the accumulated charges for respective pixels.

In the case of frame-sequential illumination, a cycle for one frame is repeated, for example, as follows: in exposure periods, only an LED of any one color is made to emit light for exposure, and in read periods, all of the LEDs are put off and an image resulting from the exposure is read. In other words, in an exposure period, for example, only the red LED 23*r* is made to emit light for exposure, and in a read period subsequent thereto, an R image obtained as a result of the red light R exposure is read, and in the following exposure period, for example, only the green LED 23*g* is made to emit light for exposure, and in a read period subsequent thereto, a G image obtained as a result of the green light G exposure is read, and in the following exposure period, for example, only the blue LED 23*b* is made to emit light for exposure, and in a read period subsequent thereto, a B image obtained as a result of the blue light B exposure is read.

Figure 4:
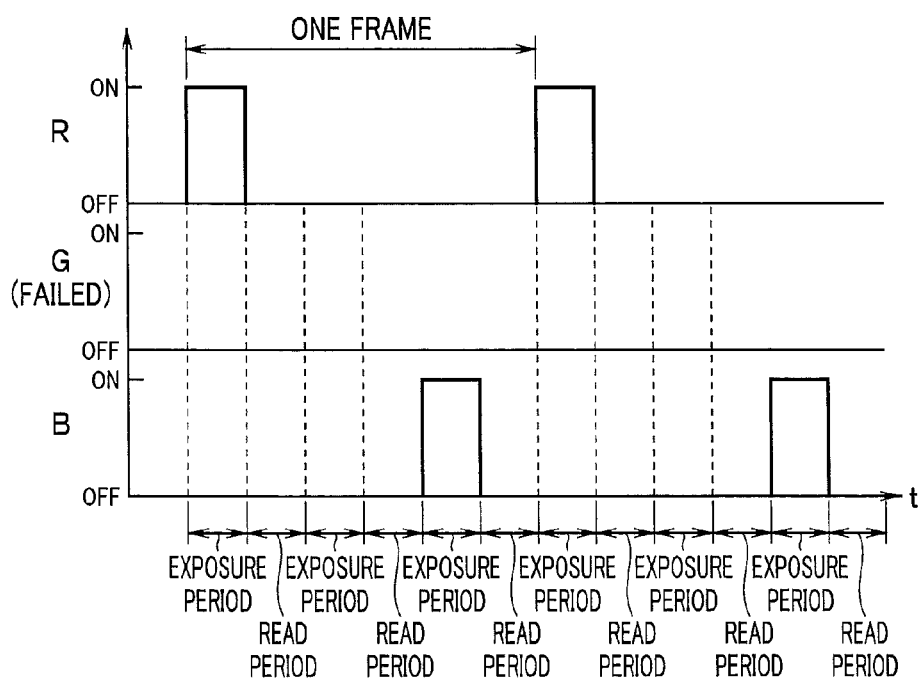
FIG. 4 is a timing chart illustrating a state of a frame-sequential illumination operation where a green LED fails in Embodiment 1.

Next, FIG. 4 is a timing chart illustrating a state of a frame-sequential illumination operation where a green LED 23*g* fails.

First, except cases where, e.g., the LED drive section 22 fails, LEDs of a plurality of colors rarely fail simultaneously and a probability of such failures may be considered sufficiently small. Therefore, cases where an LED of any one color in LEDs of a plurality of colors fails will be discussed below.

As illustrated in FIG. 4, even if, for example, a failure of the green LED 23*g* to emit light occurs, the LEDs other than the green LED 23*g* normally emit light. However, in this case, no G image can be obtained because illumination with the green light G is not provided, and if the video processor 4 performs image processing similar to that in the case of normal illumination, an image with poor color balance due to lack of G components in the RGB color image is displayed on the monitor 5.

Therefore, in the endoscope system 1 according to the present embodiment, if the control section 21 detects a failure of any LED based on an output of the color sensor 27, which is a failure detection section, the following processing is performed.

First, upon detection of a failure of any LED, the control section 21 provides an instruction to the LED drive section 22 to stop power supply to the failed LED. Accordingly, in the example illustrated in FIG. 4, power supply to the green LED 23*g* is stopped. An LED may fail not only in an open mode but also in a short mode, and in the latter case, wasteful current may flow. Accordingly, stoppage of power supply to a failed LED enables suppression of such wasteful power consumption.

Furthermore, the control section 21 notifies the video processor 4 of failed LED information (missing color information) on which color LED is in a failed state, via the communication cable 6.

Upon receipt of the failed LED information (missing color information), the video processor 4 first generates a warning indicating that an error occurs in the light source apparatus 3 and outputs the warning to the monitor 5. Consequently, on the monitor 5, the warning is displayed in such a manner that the warning can be viewed by a user. Note that in this case, e.g., information on which color LED fails and/or information for urging LED replacement may be displayed together with the warning.

Furthermore, the video processor 4 switches processing for the image signal inputted from the CCD 13 to image processing according to light emission only by the LEDs of the colors with no failure detected, which is different from that in the case where no LED failure is detected.

More specifically, when all the LEDs normally operate and no LED failure is detected, the video processor 4 performs image processing (color processing) using a color matrix (for example, a three-row, three-column matrix with three input components and three output components) for generating a color display image using inputs of an R image, a G image and a B image.

On the other hand, if the video processor 4 receives failed LED information (missing color information) from the control section 21, the video processor 4 performs image processing using a processing matrix according to the failed LED.

For example, as described above, if the video processor 4 receives failed LED information (missing color information) to the effect that the green LED 23*g* fails, the video processor 4 performs image processing (monochromatic processing) using a monochromatic matrix (for example, a one-row, two-column matrix of two input components and one output component) for generating a monochromatic display image using inputs of an R image and a B image.

Likewise, in the present embodiment, if the red LED 23*r* fails, the video processor 4 performs image processing (monochromatic processing) using a monochromatic matrix for generating a monochromatic display image using a G image and a B image, and if the blue LED 23*b* fails, the video processor 4 performs image processing (monochromatic processing) using a monochromatic matrix for generating a monochromatic display image using an R image and a G image.

Consequently, monochromatic processing in the present embodiment is processing for generating a monochromatic display image as a result of the video processor 4 performing monochromatic processing on a picked-up image according to a manner of light emission by the light source apparatus 3.

Note that although in the above description, one color sensor 27 is disposed at a position where leaked light in a light flux exiting from the condenser lens 26 is detected, the present invention is not limited to such configuration, an monochromatic illuminance sensor may be arranged in the vicinity of each of the LEDs 23r, 23g and 23b for failure detection.

Also, although in the above description, the color sensor 27 is used as a failure detection section that detects a failure of any light-emitting device, the present invention is not limited to such configuration, for example, a voltage detection section that detects a forward voltage of each of the LEDs 23r, 23g and 23b may be provided as a failure detection section to detect, e.g., shorts, opens and/or forward voltage abnormality increases in the respective LEDs 23r, 23g and 23b, in order to detect a failure based on a result of the detection.

Furthermore, although in the above description, the CCD 13, which is an image pickup device, is disposed at the distal end portion of the insertion portion of the scope 2, the present invention is not limited to such configuration, a configuration in which an optical image is transmitted via, e.g., a relay optical system and picked up on the proximal side of the scope 2, or in the video processor may be employed. Accordingly, the image pickup device is not necessarily included in the endoscope.

According to Embodiment 1 described above, even if any of light-emitting devices of a plurality of colors fails, an image with poor color balance is not displayed on the monitor 5, providing neither feeling of discomfort nor stress to a user that observes the monitor 5.

Then, a monochromatic display image is automatically displayed instead of a color display image with poor color balance, enabling the user to safely perform processing for removing the scope from the inside of a body cavity.

Furthermore, upon occurrence of an LED failure, a warning is displayed on the monitor 5 when a color display image is switched to a monochromatic display image, enabling a user to recognize the reason of the switching to the monochromatic display image.

Since the video processor 4 performs monochromatic processing according to which color LED fails, the video processor 4 can generate a monochromatic display image according to images of available colors.

[Embodiment 2]

Figure 5:
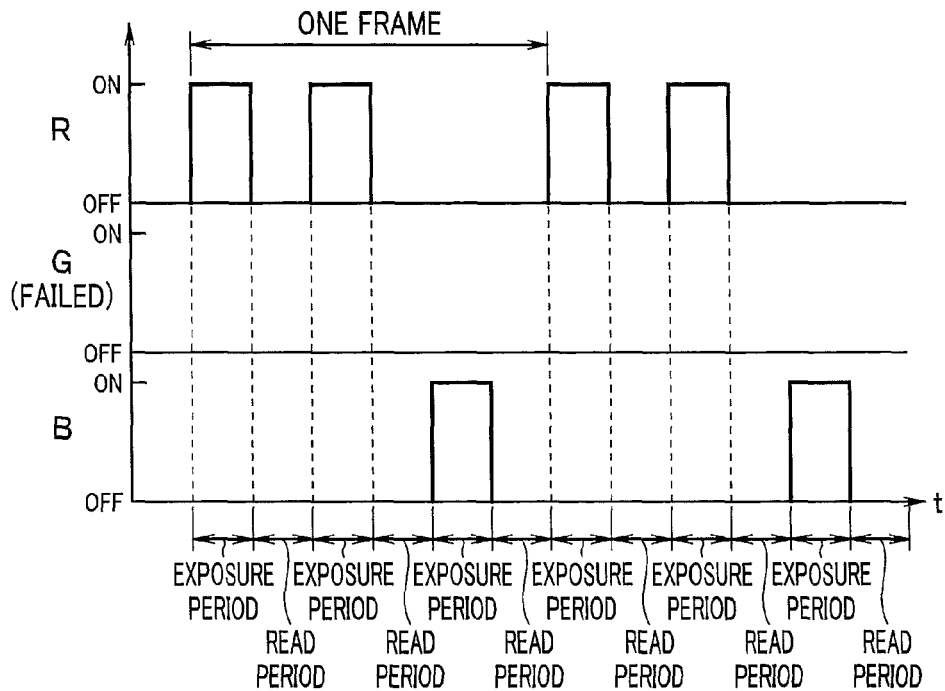
FIG. 5 is a timing chart illustrating a first example of a frame-sequential illumination operation where a green LED fails in Embodiment 2 of the present invention.
Figure 6:
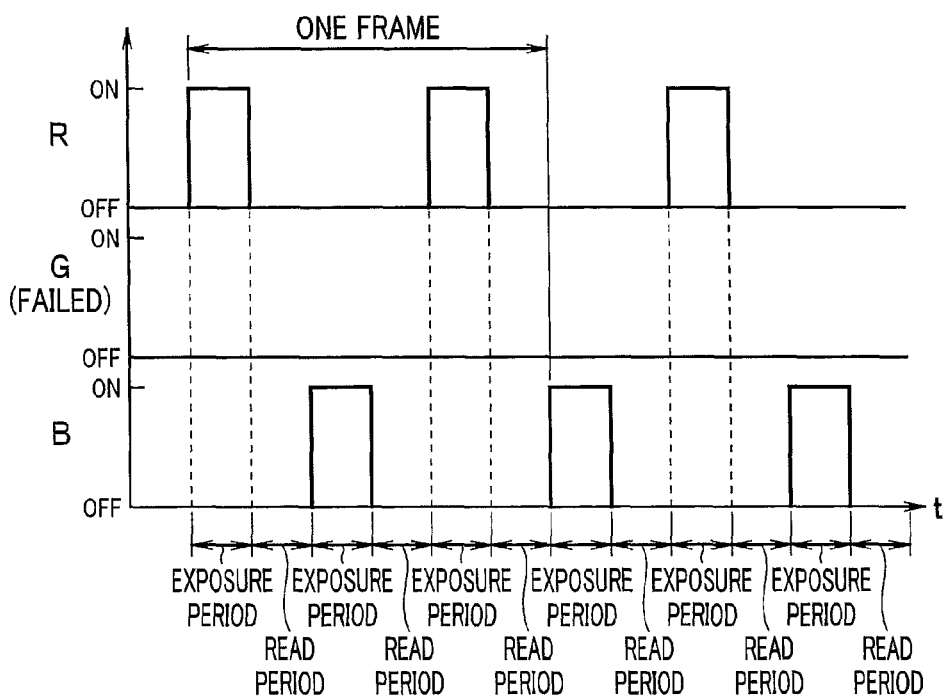
FIG. 6 is a timing chart illustrating a second example of a frame-sequential illumination operation where a green LED fails in Embodiment 2.
Figure 7:
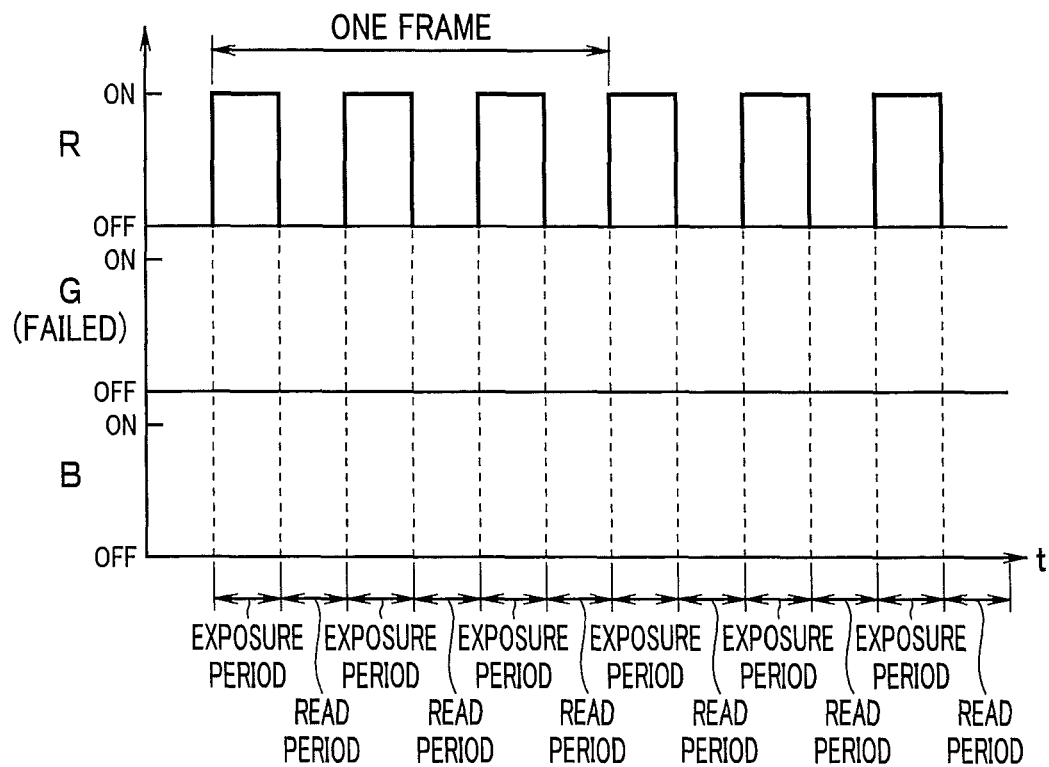
FIG. 7 is a timing chart illustrating a third example of a frame-sequential illumination operation where a green LED fails in Embodiment 2.

FIGS. 5 to 7 illustrate Embodiment 2 of the present invention: FIG. 5 is a timing chart illustrating a first example of a frame-sequential illumination operation where a green LED 23g fails, FIG. 6 is a timing chart illustrating a second example of a frame-sequential illumination operation where the green LED 23g fails; and FIG. 7 is a timing chart illustrating a third example of a frame-sequential illumination operation where the green LED 23g fails.

In Embodiment 2, parts similar to those of Embodiment 1 described above are provided with reference numerals that are the same as those of Embodiment 1, and a description will be provided mainly only on points that are different from those of Embodiment 1.

In Embodiment 1 described above, in a frame-sequential illumination operation, during each exposure period in which illumination with a failed LED is supposed to be provided, no illumination is provided because of the failure of the LED (see, e.g., FIG. 4).

On the other hand, in Embodiment 2, if a failure of an LED of any color is detected, during all of exposure periods in the CCD 13, LEDs of any one or more colors with no failure detected are made to emit light.

As illustrated in FIG. 4, an example of light emission of LEDs of other colors when a green LED 23g fails will be described with reference to FIGS. 5 to 7.

In a first example, which is illustrated in FIG. 5, during periods in which the green LED 23g emits light in the case of normal frame-sequential illumination, a red LED 23r is made to emit light instead of the green LED 23g. Also, in the first example, during respective frame-sequential periods in which the red LED 23r and a blue LED 23b are made to emit light in a normal case where no failure occurs, there is no change even if the green LED 23g fails.

In this case, the video processor 4 performs image processing (monochromatic processing) using a monochromatic matrix for generating a monochromatic display image using inputs of an R image, an R image and a B image. The monochromatic matrix used here may be a one-row, three-column matrix with three input components (R component, R component and B component) and one output component (monochromatic component (luminance component)), or a one-row, two-column matrix with two input components (average R component and B component) and one output component (monochromatic component (luminance component)) may be used after averaging of two R images in one frame.

Where the processing illustrated in FIG. 5 is performed, it is advantageous that even during occurrence of an abnormality in which the green LED 23g fails, there is no need to change procedures for light emission of the red LED 23r and the blue LED 23b in normal frame-sequential illumination and image processing procedures for an R image and a B image in normal frame-sequential illumination.

Also, in a second example, which is illustrated in FIG. 6, where any of the LEDs fails, instead of continuously using a light emission sequence in normal frame-sequential illumination operation as a base, LEDs that can emit light are made to alternately emit light during exposure periods of the CCD 13. In other words, in an example in which the green LED 23g fails, the red LED 23r and the blue LED 23b are made to alternately emit light in exposure periods of the CCD 13.

In this case, images obtained in a certain frame are an R image, a B image and an R image, but images obtained in the following frame are a B image, an R image and a B image. Accordingly, the video processor 4 may change monochromatic matrix for use for each frame to use a one-row, three-column matrix with three input components (R component, B component and R component) and one output component (monochromatic component (luminance component)) in the former case, and use a one-row, three-column matrix with three input components (B component, R component and B component) and one output component (monochromatic component (luminance component)) in the latter case. Alternatively, an average R component or an average B component may be calculated for each frame so that a same monochromatic matrix (one-row, two-column matrix with two input components [(average R component and B component) or (R component and average B component)] and one output component (monochromatic component (luminance component))) can be used.

Where the processing illustrated in FIG. 6 is performed, a light emission halt period is provided to each of LEDs of colors in which light can be emitted (in other words, when an LED of one color emits light, an LED of the other color is in a light emission halt period), providing advantages of suppressing successive LED lighting to prevent heating, enabling an increase in lifetime of the LEDs.

Furthermore, in a third example, which is illustrated in FIG. 7, when any of LEDs fails, only an LED of any one of colors in which light can be emitted is made to emit light during all of exposure periods of the CCD 13. The example illustrated in FIG. 7 is an example in which the red LED 23r from among the red LED 23r and the blue LED 23b that can emit light is made to emit light in all of exposure periods of the CCD 13. Here, although the blue LED 23b can be made to emit light in all of exposure periods of the CCD 13 instead of the red LED 23r, when any one color is selected from LEDs that can emit light, it is favorable to consider the following points. First, there are LEDs with high emission efficiency and LEDs with low emission efficiency. Accordingly, it is favorable to select an LED with higher emission efficiency from among LEDs that can emit light. Furthermore, a monochromatic CCD 13 has a charge generation efficiency depending on a wavelength band. Accordingly, it is favorable to select an LED that emits light in a wavelength band that provides high charge generation efficiency from among LEDs that can emit light.

Then, in the third example, the video processor 4 only needs to use a one-row, three-column matrix with three input components (R component, R component and R component) and one output component (monochromatic component (luminance component)) or a one-row, one-column matrix with one input component (average R component) and one output component (monochromatic component (luminance component)) (however, in this case, the processing is coefficient multiplication processing rather than that using a matrix).

The processing illustrated in FIG. 7 provides the advantage of simplification of image processing by the video processor 4.

Also, the present invention is not limited to the examples illustrated in FIGS. 5 to 7, and it is possible that if any of LEDs fails, all of LEDs that can emit light are made to emit light during exposure periods of the CCD 13. In this case, in FIG. 7, not only the red LED 23r emits light in all of exposure periods of the CCD 13, but also the blue LED 23b emits light simultaneously.

In this case, the video processor 4 may use a one-row, three-column matrix with three input components ((R+B) component, (R+B) component and (R+B) component) and one output component (monochromatic component (luminance component)) or a one-row, one-column matrix with one input component (average (R+B) component) and one output component (monochromatic component (luminance component)). In this case, also, the advantages of simplification of image processing by the video processor 4 and obtainment of a bright image can be provided.

As described above, monochromatic processing according to the present embodiment is also processing for generating a monochromatic display image as a result of the video processor 4 performing monochromatic processing on a picked-up image according to a manner of light emission by the light source apparatus 3.

According to Embodiment 2, effects substantially similar to those of Embodiment 1 described above are provided and illuminating light is emitted in all of exposure periods of the CCD 13, and thus, there is no waste in operation of the CCD 13 in the exposure periods and the read periods. In addition, a monochromatic display image is created based on image signals obtained in all of the exposure periods, providing the advantage of provision of a brighter monochromatic display image with a high S/N ratio.

[Embodiment 3]

Figure 8:
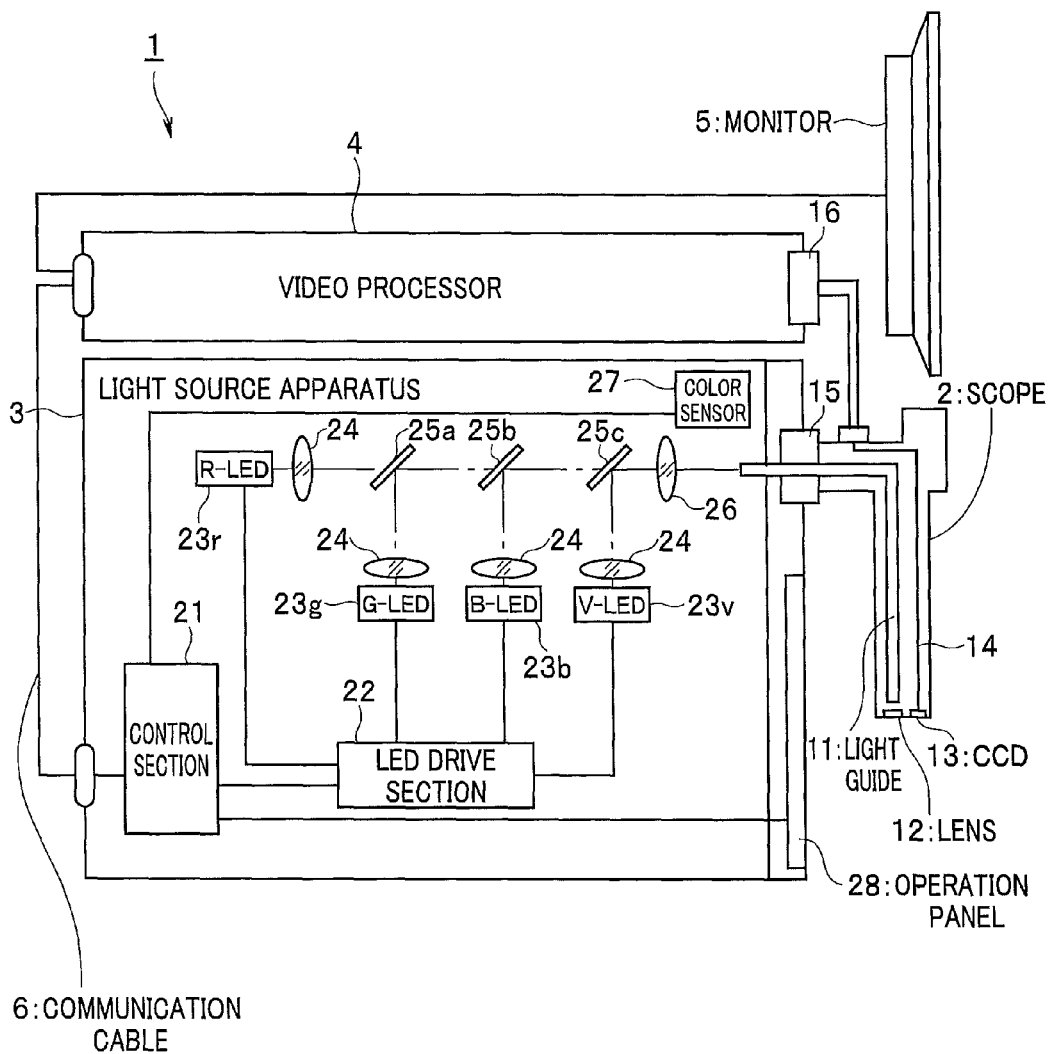
FIG. 8 is a diagram illustrating a configuration of an endoscope system according to Embodiment 3 of the present invention.
Figure 9:
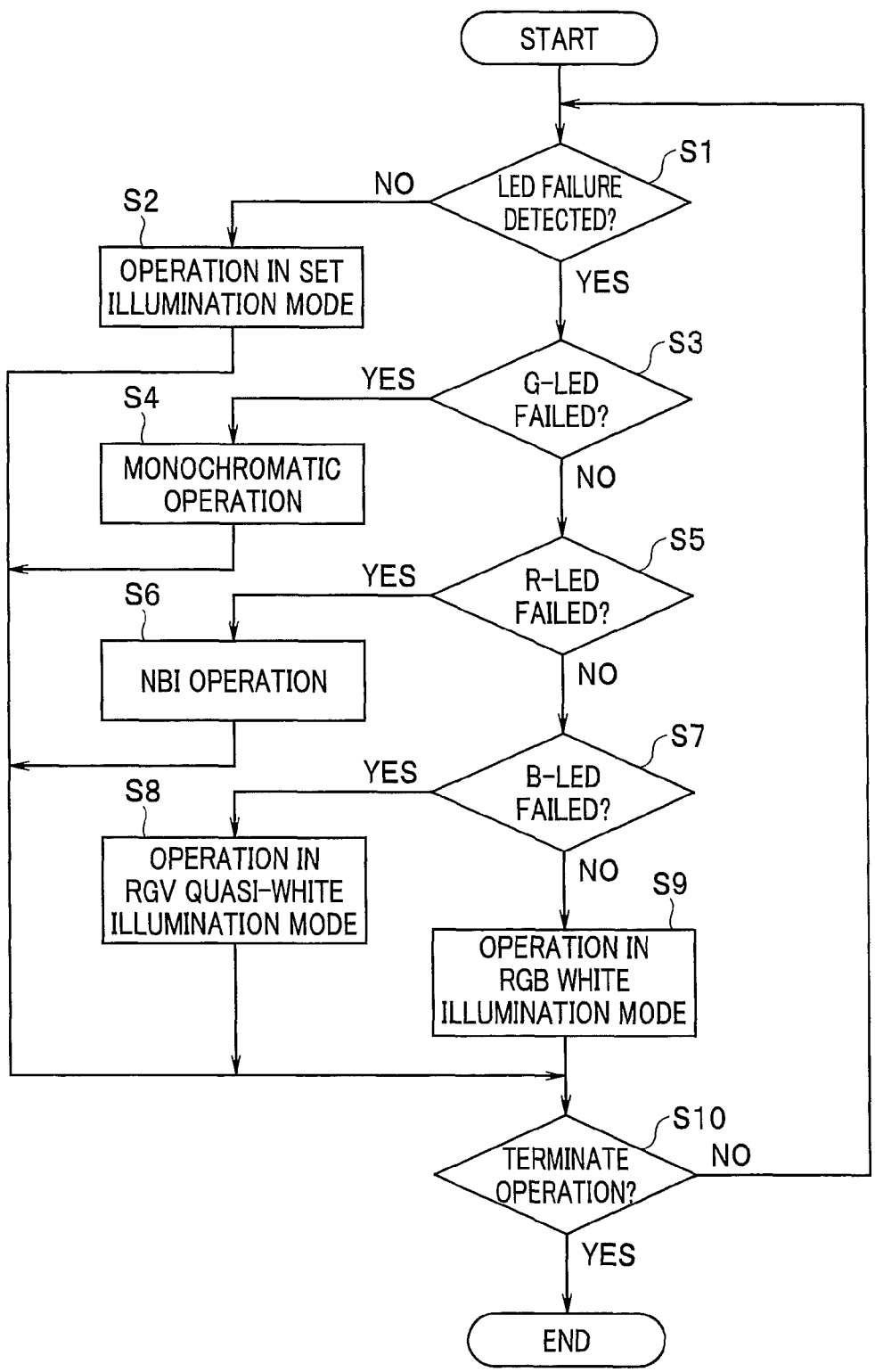
FIG. 9 is a flowchart illustrating processing for changing an illumination mode of an operation according to a color of a failed LED in Embodiment 3.
Figure 10:
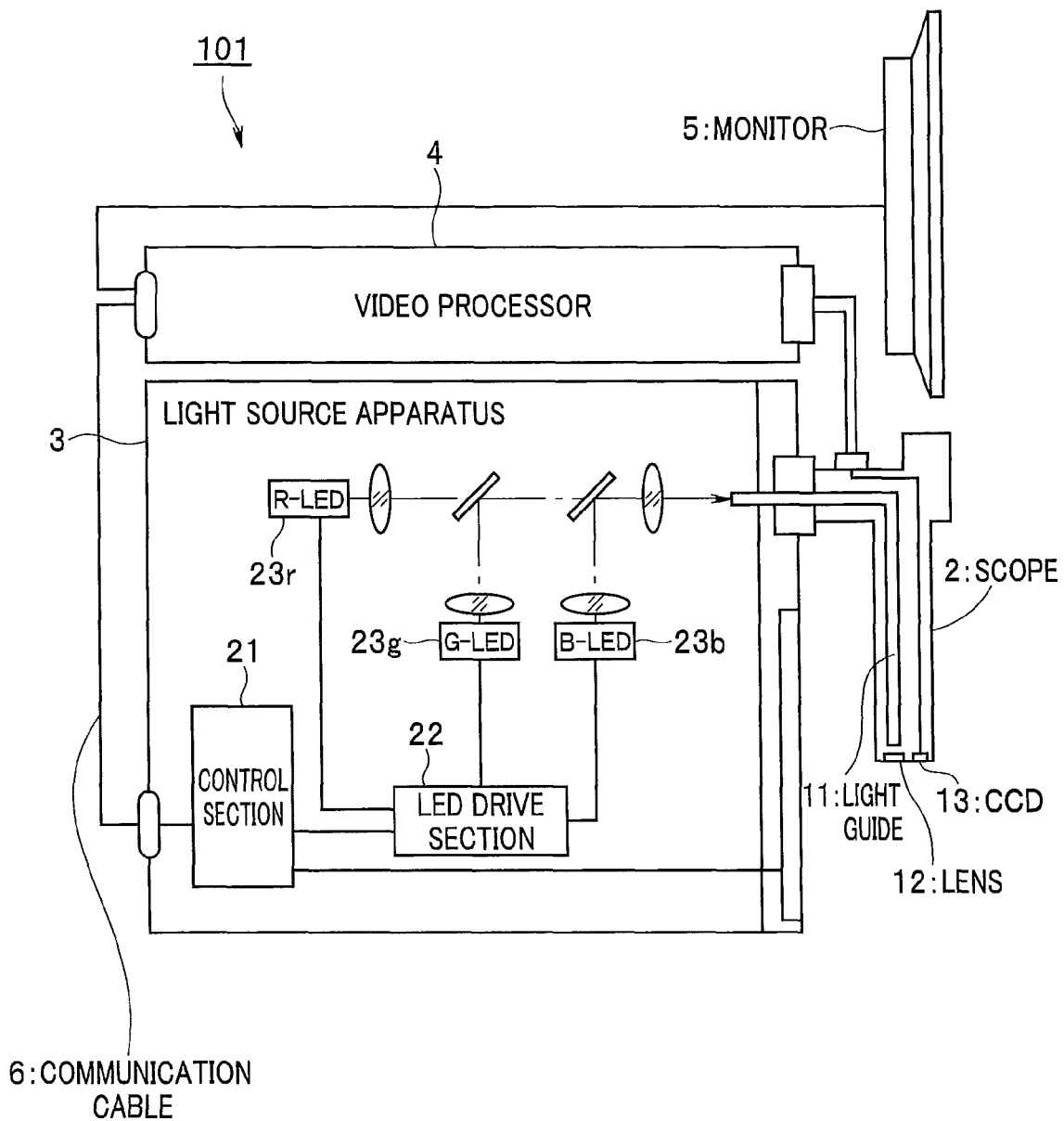
FIG. 10 is a diagram illustrating a configuration of a conventional endoscope system using LEDs as light sources.

FIGS. 8 and 9 illustrate Embodiment 3 of the present invention, and FIG. 8 is a diagram illustrating an endoscope system.

In Embodiment 3, parts similar to those of embodiments 1 and 2 described above are provided with reference numerals that are the same as those of embodiments 1 and 2, and a description thereof will be omitted, and a description will be provided mainly only on points that are different from embodiments 1 and 2.

In an endoscope system 1 according to the present embodiment, a violet LED 23v, which is a narrow band V (violet) light-emitting device, is further provided to the configuration illustrated in FIG. 1 in Embodiment 1, as a narrow band light-emitting device for emitting narrow band light. With the addition of the violet LED 23v, another collimator lens 24 and a third dichroic filter 25c are added to the optical system.

It is known that upon irradiation with light having wavelengths in a narrow band that is easily absorbed by hemoglobin in blood, blood vessels can be observed in such a manner that the blood vessels are highlighted. The violet LED 23v added in the present embodiment is provided for performing such narrow band light observation (Narrow Band Imaging: NBI (registered trademark)), emitting narrow band light with wavelengths of, for example, 390 to 445 nm. When narrow band light observation using the violet LED 23v is performed, for example, capillary vessels in a superficial layer of a mucous membrane can be observed in such a manner that capillary vessels are highlighted. Also, it is known that if observation using narrow band light with wavelengths of 530 to 550 nm is performed, a contrast between observation of thick blood vessels in a deep part and capillary vessels in a superficial layer of a mucous membrane can be emphasized. Therefore, the green LED 23g in the present embodiment emits such narrow band light, and thus, doubles as a narrow band light-emitting device.

Accordingly, the endoscope system 1 according to the present embodiment can set a white light observation mode and a narrow band light observation mode as observation modes for normal operation. Along with that, a light source apparatus 3 is configured to perform operation in a white illumination mode for the white light observation mode, and perform operation in a narrow band illumination mode for the narrow band light observation mode.

In the white illumination mode, all of the red LED 23r, the green LED 23g, the blue LED 23b and the violet LED 23v emit light. Here, when frame-sequential illumination is provided, the red LED 23r emits light in a first field in one frame, the green LED 23g emits light in a second field, and the blue LED 23b and the violet LED 23v emit light in a third field. Employment of such light emission manner enables an amount of light emission of the blue LED 23b to be supplemented by light emission of the violet LED 23v.

Also, in the white light observation mode corresponding to the white illumination mode in the light source apparatus 3, the video processor 4 performs image processing for generating a white light observation image, using a color matrix. Here, the color matrix used in the white light observation mode in the present embodiment is, for example, a three-row, three-column matrix with three input components (R component, G component and (B+V) component) and three output components (R component, G component and B component).

On the other hand, in the narrow band illumination mode, the violet LED 23v and the green LED 23g emit light.

In the narrow band light observation mode corresponding to the narrow band illumination mode in the light source apparatus 3, the video processor 4 performs image processing for generating a narrow band light observation image, using, e.g., a color matrix for narrow band light. Here, the color matrix for narrow band light is, for example, a three-row, two-column matrix with two input components (G component and V component) and three output components (R component, G component and B component). In other words, even if color components of two colors are obtained from the CCD 13, an image displayed on a monitor 5 in the narrow band light observation mode is a color display image based on three colors.

Note that aside from the observation modes for normal operation, the endoscope system 1 may be set in any of observation modes for emergency when a failure occurs in an LED, which will be descried later with reference to FIG. 9, and in response to that, the light source apparatus 3 performs operation in a corresponding illumination mode for emergency.

The added collimator lens 24 is disposed on an optical path of light emitted from the violet LED 23v, and makes incoming light exit in the form of collimated light.

The third dichroic filter 25c transmits red light R from the red LED 23r, green light G from the green LED 23g and blue light B from the blue LED 23b, and reflects narrow band light from the violet LED 23v.

Next, FIG. 9 is a flowchart illustrating processing for changing an illumination mode of an operation according to a color of a failed LED. The processing is mainly performed by a control section 21 in the light source apparatus 3.

Upon start of the processing, the control section 21 determines whether or not a failure occurs in any of the LEDs, based on inputs from the color sensor 27 (step S1).

Here, if it is determined that no LED failure occurs, the control section 21 controls the light source apparatus 3 to operate in an illumination mode corresponding to an observation mode for normal time, which is set in the endoscope system 1 (step S2).

Also, if it is determined in step S1 that a failure occurs in any of the LEDs, the control section 21 determines whether or not the failed LED is the green LED 23g (step S3).

Here, if it is determined that the failed LED is the green LED 23g, the control section 21 stops power supply to the green LED 23g, via the LED drive section 22, and controls the light source apparatus 3 to operate in a monochromatic illumination mode corresponding to a monochromatic observation mode for emergency (step S4). Where the green LED 23g fails, not only the white illumination mode cannot be set, but also it is difficult to provide color reproduction close to white illumination and furthermore, the narrow band light observation mode cannot be set, and thus, the monochromatic illumination mode is set. In the monochromatic illumination mode, the LEDs other than the green LED 23g are made to emit light (for the light emission manner, see, e.g., Embodiment 1 described above).

In this case, as in Embodiment 1 described above, the video processor 4 is notified of failed LED information (missing color information), a warning is displayed and the image processing is switched to image processing for generating a monochromatic display image according to a manner of light emission by the light source apparatus 3.

If it is determined in step S3 that the failed LED is not the green LED 23g, the control section 21 determines whether or not the failed LED is the red LED 23r (step S5).

Here, if it is determined that the failed LED is the red LED 23r, the control section 21 stops power supply to the red LED 23r, via the LED drive section 22, and controls the light source apparatus 3 to operate in the narrow band illumination mode (step S6). Where the red LED 23r fails, operation in the white illumination mode cannot be performed, but operation in the narrow band illumination mode can be performed. Therefore, even if observation using normal white illuminating light is performed until a failure is detected, here, the illumination mode is switched to the narrow band illumination mode.

In this case, also, the video processor 4 is notified of failed LED information (missing color information), a warning is displayed and the image processing is switched to image processing for narrow band illumination for generating a narrow band light observation image (image processing using, e.g., a color matrix for narrow band light, which has been described above).

If it is determined in step S5 that the failed LED is not the red LED 23r, the control section 21 determines whether or not the failed LED is the blue LED 23b (step S7).

Here, if it is determined that the failed LED is the blue LED 23b, the control section 21 stops power supply to the blue LED 23b, via the LED drive section 22, and controls the light source apparatus 3 to operate in an RGV quasi-white illumination mode corresponding to an RGV quasi-white observation mode for emergency (step S8). Here, the RGV quasi-white illumination mode is an illumination mode in which instead of both the blue LED 23b and the violet LED 23v being made to emit light in the white illumination mode for normal time as described above, only the violet LED 23v is made to emit light during the relevant light emission periods.

A light emission band of the violet LED 23v is a band close to violet, but if the visible broadband is roughly segmented into three bands, R, G and B, the light emission band of the violet LED 23v falls within the B band in a broad sense. Accordingly, even if RGV illumination is provided, illumination with a color close to white, which is equivalent to RGB illumination, can be provided. However, in this case, in order to compensate for lack of an amount of light emission from the blue LED 23b, it is necessary to increase an amount of light emission from the violet LED 23v, and the amount of light emission of the violet LED 23v is made to be, for example, a maximum unless the maximum light emission amount of the violet LED 23v is considerably large. Note that where the amount of light emission is insufficient even though the maximum light emission amount is provided, the amounts of light emission of the red LED 23r and the green LED 23g may be maintained as they are, placing emphasis on the brightness of the image, or the amount of light emission of the red LED 23r and the green LED 23g may be decreased according to the maximum light emission amount of the violet LED 23v, placing emphasis on the color balance of the image.

In this case, also, the video processor 4 is notified of failed LED information (missing color information), a warning is displayed, the image processing is switched to image processing for generating a quasi-white light observation image close to a white light observation image to the possible extent, according to RGV quasi-white illumination (image processing using, e.g., a color matrix for RGV quasi-white light). Here, the color matrix for RGV quasi-white light is, for example, a three-row, three-column matrix with three input components (R component, G component and V component) and three output components (R component, G component and B component). Accordingly, an image displayed on the monitor 5 in the RGV quasi-white illumination mode is a color display image based on the three colors.

If it is determined in step S7 that the failed LED is not the blue LED 23b, the control section 21 determines that the failed LED is the violet LED 23v, the control section 21 stops power supply to the violet LED 23v, via the LED drive section 22, and controls the light source apparatus 3 to operate in the RGB white illumination mode corresponding to an RGB white observation mode for emergency (step S9). Here, the RGB white illumination mode is an illumination mode in which instead of both the blue LED 23b and the violet LED 23v being made to emit light in the white illumination mode for normal time as described above, only blue LED 23b is made to emit light in the relevant light emission periods.

Where all of R light, G light and B light are provided, white illumination can be provided in principle. However, in this case, in order to compensate for lack of an amount of light from the violet LED 23v, it is necessary to increase the amount of light emission of the blue LED 23b. If the light amount is insufficient even when a maximum light emission amount is provided, the amounts of light emission of the red LED 23r and the green LED 23g may be maintained as they are, placing emphasis on the brightness of the image (in other words, not pure white illumination, but quasi-white illumination is provided) and the amounts of light emission of the red LED 23r and the green LED 23g may be decreased according to the maximum light emission amount of the blue LED 23b, placing emphasis on the color balance of the image.

In this case, the video processor 4 is notified of failed LED information (missing color information), a warning is displayed, and switching to the narrow band light observation mode is prohibited and the image processing is switched to image processing for generating a white light observation image according to RGB white illumination (image processing using, e.g., a color matrix for RGB white light). Here, the color matrix for RGB white light is, for example, a three-row, three-column matrix with three input components (R component, G component and B component) and three output components (R component, G component and B component). Accordingly, an image displayed on the monitor 5 in the RGB white illumination mode is a color display image based on the three colors. Then, even if narrow band light observation is performed until the failure is detected, the observation mode is switched to the RGB white observation mode after the failure detection.

Subsequently, the control section 21 determines whether or not to terminate the operation (step S10), if it is determined not to terminate the operation, the process is returned to step S1 and processing such as described above is repeated, and if it is determined to terminate the operation, the processing is terminated.

Embodiment 3 described above provides effects substantially similar to those of embodiments 1 and 2 described above and enables provision of proper illumination for emergency according to a color of a failed LED.

For example, even if the violet LED 23v fails, RGB white illumination can be provided, enabling observation using white illumination close to white illumination for normal time.

Also, even if the blue LED 23b fails, observation using quasi-white illumination equivalent to white illumination for normal time can be performed.

Furthermore, even if the red LED 23r fails, observation using narrow band illumination can be performed because operation in the narrow band light observation mode, which is similar to that for normal time, can be performed.

It is sufficient that only if the green LED 23g fails, the observation mode is inevitably switched to the monochromatic observation mode.

As described above, in the present embodiment, because of addition of the violet LED 23v for narrow band observation, in the case of an emergency in which an LED failure occurs, observation to provide an image close to a color display image for normal time, rather than a monochromatic display image, can be performed depending on a color of the failed LED.

Note that although the above description has been provided mainly on an endoscope system, a method for controlling an endoscope system in such a manner as described above may be provided, and, e.g., a control program for making a computer control an endoscope system in such a manner as described above and/or a computer-readable recording medium that records such control program may be provided.

Also, the present invention is not limited directly to the above-described embodiments, and can be embodied with any of components thereof modified without departing from the spirit of the present invention in practical phase. Also, a proper combination of a plurality of components disclosed in the embodiments enables formation of various aspects of the invention. For example, some components may be deleted from all the components indicated in the embodiments. Furthermore, components in different embodiments may be combined as appropriate. As described above, it should be understood that various modifications and applications are possible without departing from the spirit of the invention.

What is claimed is:

1. An endoscope system comprising:
    a light source apparatus comprising a first light-emitting device that generates light of a first color,
    a second light-emitting device that generates light of a second color different from the first color,
    a failure detection section that detects which color light-emitting device fails in the first light-emitting device and the second light-emitting device, and
    a light source control section that controls, when a failure of the first light-emitting device or the second light-emitting device is detected by the failure detection section, the first and second light-emitting devices to generate illumination light by the light-emitting device other than the light-emitting device for which the failure is detected in the first and second light-emitting devices;
    an endoscope that irradiates a subject with illuminating light generated by the light source apparatus and takes in an optical image of the subject;
    an image pickup device that picks up an image of the optical image of the subject;
    a video processor that processes the image picked up by the image pickup device;
    a selecting section that selects, based on a detection result by the failure detection section, image processing in the video processor from among color image processing corresponding to a state in which a failure does not occur in the first and second light-emitting devices, first image processing corresponding to a failure of the first light-emitting device, and second image processing corresponding to a failure of the second light-emitting device; and
    a monitor that displays the image subjected to the image processing selected by the selecting section.

2. The endoscope system according to claim 1, further comprising a third light-emitting device that generates light of a third color which is different from the first and second colors,
    wherein the failure detection section further detects a failure of the third light-emitting device,
    the light source control section controls the first to third light-emitting devices to generates the illumination light by the light-emitting device other than the light-emitting device for which a failure is detected from among the first to third light-emitting devices, and the selecting section selects, based on a detection result by the failure detection section, the image processing by the video processor from among the color image processing, the first image processing, the second image processing, and third image processing corresponding to a failure of the third light-emitting device.

3. The endoscope system according to claim 2,
wherein the first to third light-emitting devices emit light of three colors forming white light.

4. The endoscope system according to claim 3,
wherein the first light-emitting device is a red light-emitting device that emits red (R) light as the first color,
the second light-emitting device is a green light-emitting device that emits green (G) light as the second color,
the third light-emitting device is a blue light-emitting device that emits blue (B) light as the third color, and
if the light-emitting device for which a failure is detected by the failure detection section is the green light-emitting device alone, the light source apparatus makes light-emitting devices other than the green light-emitting device emit light and the video processor performs monochromatic processing on the picked-up image according to a manner of light emission by the light source apparatus to generate a monochromatic display image.

5. The endoscope system according to claim 4, further comprising a narrow band light-emitting device that emits narrow band light,
wherein if the light-emitting device for which a failure is detected by the failure detection section is the narrow band light-emitting device alone, an illumination mode is set to an RGB white illumination mode and the light source apparatus provides RGB white illumination, the selecting section selects the image processing in accordance with the RGB white illumination, and the video processor performs the selected image processing on the picked-up image to generate a color display image.

6. The endoscope system according to claim 5,
wherein the narrow band light-emitting device includes a narrow band violet (V) light-emitting device; and
wherein if the light-emitting device for which a failure is detected by the failure detection section is the blue light-emitting device alone, the illumination mode is set to an RGV quasi-white illumination mode, the light source apparatus makes only the violet light-emitting device emit light during a period in which the blue light-emitting device is made to emit light, to provide RGV quasi-white illumination, the selecting section selects the image processing in accordance with the RGV quasi-white illumination, and the video processor performs the selected image processing on the picked-up image to generate a color display image.

7. The endoscope system according to claim 6,
wherein the green light-emitting device doubles as the narrow band light-emitting device; and
wherein if the light-emitting device for which a failure is detected by the failure detection section is the red light-emitting device alone, the illumination mode is set to a narrow band illumination mode and the light source apparatus makes the violet light-emitting device and the green light-emitting device emit light to provide narrow band illumination, and the video processor performs image processing for narrow band illumination on the picked-up image to generate a narrow band image.

8. The endoscope system according to claim 3,
wherein if no failure of the light-emitting devices is detected, the light source apparatus provides frame-sequential illumination using the light-emitting devices that emit the light of three colors forming white light, and if a failure of a light-emitting device of any of the colors is detected, the light source apparatus makes a light-emitting device of at least any one color for which no failure is detected emit light in all exposure periods of the image pickup device; and
wherein if a failure of any of the light-emitting devices is detected by the failure detection section, the video processor performs monochromatic processing on the picked-up image according to a manner of light emission by the light source apparatus to generate a monochromatic display image.

* * * * *